United States Patent [19]

Toulhoat et al.

[11] Patent Number: 4,837,158

[45] Date of Patent: Jun. 6, 1989

[54] PROCESS FOR CHARACTERIZING A CATALYST BY DETERMINATION OF ITS CONVERSION AND COKING ACTIVITIES

[75] Inventors: Hervé Toulhoat, Houilles; Anne Favre, Poissy, both of France

[73] Assignee: Institut Francais du Petrole, Rueil-Malmaison, France

[21] Appl. No.: 53,666

[22] Filed: May 26, 1987

[30] Foreign Application Priority Data

May 27, 1986 [FR] France ................... 86 07690

[51] Int. Cl.$^4$ ............... G01N 25/22; G01N 31/10
[52] U.S. Cl. ........................ 436/37; 436/159
[58] Field of Search ............ 422/130; 436/34, 35, 436/37, 159

[56] References Cited

U.S. PATENT DOCUMENTS

| | | | |
|---|---|---|---|
| 4,099,923 | 7/1978 | Milberger . | |
| 4,419,328 | 12/1983 | Walsh | 436/37 |
| 4,425,259 | 1/1984 | Hettinger et al. | 208/120 |
| 4,568,426 | 2/1986 | Orlando . | |

FOREIGN PATENT DOCUMENTS 0026012  1/1981  European Pat. Off. .

OTHER PUBLICATIONS

Hindin et al., Analytical Chemistry, vol. 29, No. 12, 12/57, pp. 1850–1852.

Primary Examiner—Barry S. Richman
Assistant Examiner—Lyle-Alfandary Alexander
Attorney, Agent, or Firm—Millen & White

[57] ABSTRACT

For characterizing a catalyst, particularly a catalyst useful in refining of oil residues, by determination of its conversion and coking activities, the steps of:
(a) impregnating the catalyst with a hydrocarbon mixture,
(b) heating the impregnated catalyst, at a rate of temperature increase ranging from 2° C./min to 50° C./sec, under inert gas in a furnace. up to a temperature $\theta_2$ ranging from 300° C. to 380° C. and measuring, by means of a hydrocarbon detector 4, a signal Q representative of the hydrocarbons generated during step b,
(c) continuing the heating under the inert gas up to a temperature $\theta_3$ ranging from 500° C. to 1000° C. and measuring, by means of detector 4, a signal P representative of hydrocarbons generated during step c,
(d) subjecting the residue to a combustion in another furnace 6 and determining a combustion signal R, by means of a suitable detector 11, and
(e) deducing from signals Q, P and R the conversion and coking activities of the catalyst.

16 Claims, 2 Drawing Sheets

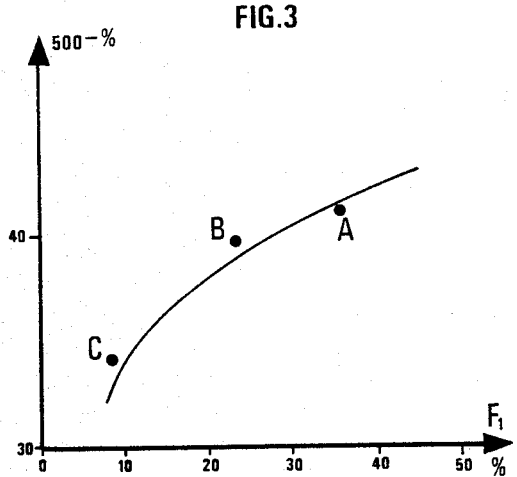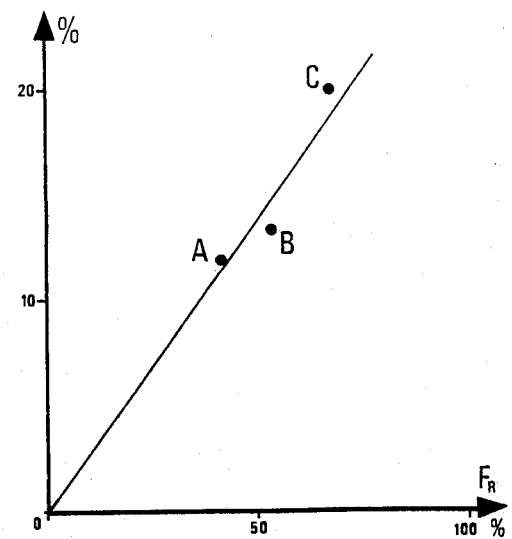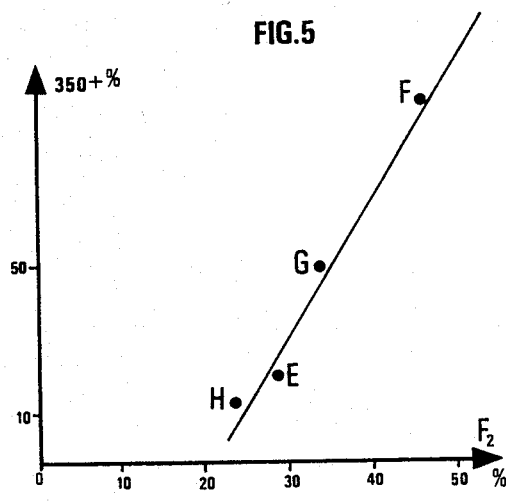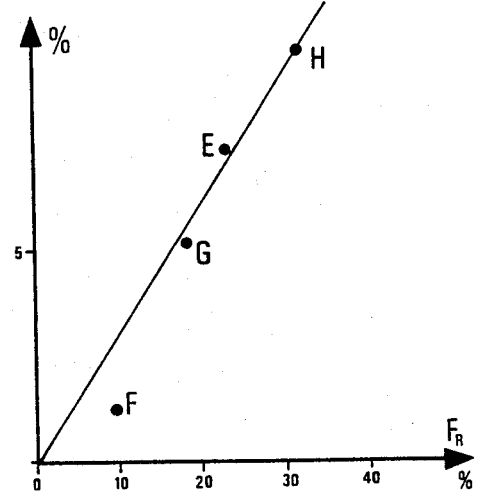

PROCESS FOR CHARACTERIZING A CATALYST BY DETERMINATION OF ITS CONVERSION AND COKING ACTIVITIES

The present invention concerns a process for characterizing a catalyst by determination of its conversion and coking activities. More particularly, the process provides for the characterization of catalysts for refining, in particular, oil residues, this catalyst being either fresh or used.

BACKGROUND OF THE INVENTION

In the field of oil refining, the catalysts have preferably a more or less high converting activity which, after periods of use, tends to decrease while the coking activity continually increases.

These catalysts may be classified in two groups, respectively concerning the fields of catalytic cracking and hydrotreatment, respectively.

For characterizing cracking catalysts, it is known to use the so-called M.A.T. test (Micro Activity test) described in standard ASTM D 39-07. This method is time-consuming since it requires, in order to obtain a balance, an intermediate simulated distillation over a chromatography column and an ex-situ analysis of the residual coke over a carbon analyzer, making it difficulty reproducible.

The tests for characterizing hydrotreatment catalysts are conducted under high pressure in the presence of hydrogen, followed by elementary analysis. Such tests are very costly and usually last about fifteen days, as a whole.

From the information obtained by these costly and time-consuming tests, the catalyst activity may be identified as a more or less converting activity and correspondingly a more or less coking activity.

The prior art is particularly illustrated by U.S. Pat. No. 4,568,426, EP No. 0 026 012 and U.S. Pat. No. 4,099,923.

U.S. Pat. No. 4,568,426 discloses a sophisticated apparatus adapted to reproduce with accuracy and simplicity the measurement of Conradson carbon (CCR) obtained by heating the sample in inert atmosphere, purging the gaseous products in an inert atmosphere and weighing the residue.

EP No. 0,026,012 discloses a method for determining the API density of an oil by vaporization of volatile and pyrolyzable compounds and by measurement of the hydrocarbon amount within a temperature range of for example 350°–750° C., in proportion to the total vaporized amount.

Finally, U.S. Pat. No. 4,099,923 discloses a unit for catalyst preselection in the presence of hydrocarbons alone or in the presence of ammonia or air or of both gases. An aliquot part of the reaction gas is separated from solids and liquids and transferred to a gas chromatograph where it is analyzed.

OBJECTS OF THE INVENTION

One object of the invention is to provide a rapid, simple, cheap and integrated, hence repeatable, process for characterizing catalysts from information which is not necessarily the same information as that used in the prior art.

Another object of the invention is to determine from a reference feed stock the converting activity of catalysts by a survey of the distribution of the obtained light products and pyrolysis products, as well as their coking activity, i.e. their deactivation potential by coking, by distribution of pyrolysis and coking products of said charge. Otherwise stated, the object is to quickly classify the catalytic materials in relation with the conversion and coking rates of heavy products.

Another object is to determine the behavior of a given catalyst in the presence of different charges and hence to predict the economic valuation potential of said charges.

Another object of the invention is to provide a catalyst whose properties can be quickly adjusted to the properties of the feed charge.

SUMMARY OF THE INVENTION

The process according to the invention thus concerns the characteristization of a catalyst by determination of its conversion and coking activities. It comprises the following successive steps of: (a) impregnating the catalyst with a hydrocarbon mixture (or charge), (b) heating the impregnated catalyst in a stream of inert gas up to a temperature $\theta_2$ ranging from 300° C. to 380° C. so as to produce a conversion evaporation during this step of temperature increase, giving a conversion- evaporation effluent, (c) subjecting said conversion - evaporation effluent, during the heating step, to a measurement, with a hydrocarbon detector, of a signal Q representative of the hydrocarbons generated during said conversion -evaporation step, (d) progressively increasing the temperature from $\theta_2$ to a value $\theta_3$ ranging from 500° C. to 1000° C., under an inert gas stream, so that pyrolysis occurs during said heating step, thus producing a pyrolysis effluent and a residue, (e) subjecting said pyrolysis effluent, during a heating step, to the measurement, by means of a hydrocarbon detector, of a signal P representative of pyrolyzed hydrocarbons generated during said pyrolysis step, (f) then subjecting said residue to a conversion at a temperature $\theta_4$ ranging from 500° C. to 1500° C., under a stream of oxidizing gas, said combustion producing a combustion gas effluent, (g) subjecting said combustion gas effluent, by means of at least one suitable detector, to a measurement of a signal R representative of the residue amount, and (h) deducing from said measured values of signals Q, P and R the conversion and coking activities of said catalyst.

The operation will generally be conducted in the presence of the same charge for a comparative survey of different catalysts or in the presence of the same catalyst for a comparative survey of different charges, all the operating conditions being otherwise unchanged.

According to the invention, hydrocarbon mixture means compounds comprising carbon and hydrogen but which may also comprise oxygen, sulfur and nitrogen. The hydrocarbon mixture corresponds for example to cuts having an initial boiling point, under normal atmospheric pressure, at least equal to 350° C. A small portion of hydrocarbons having a boiling point lower than 350° C. may be tolerated, althrough it is not desirable.

The relevant catalysts are, for example, those used in refining processes, particularly those used for catalytic cracking or hydrotreatments.

According to a particular embodiment, a specific carbon dioxide detector may be used to measure a signal representative of a carbon dioxide amount resulting from the combustion, and consequently of the residue amount. But, when the presence, after the combustion step, of sulfur and/or nitrogen oxides is usefully taken into account for the survey of a charge of high sulfur and/or nitrogen content, several appropriate detectors for these oxides can be combined in series or a single infrared multichannel detector used, for example, to obtain a signal R representative of the amounts of carbon dioxide, sulfur oxide and nitrogen oxide and hence of the amount of said residue.

Before the heating step, all the catalyst is impregnated by the hydrocarbon mixture. This impregnation is conducted as homogeneously as possible, preferably with a solution in a solvent of boiling point much lower than the initial boiling point of the hydrocarbon mixture, so that it can be removed without stripping all or part of the mixture. Advantageously a light aromatic solvent, preferably an alkylbenzene, will be used to dissolve asphaltenes. The hydrocarbon mixture concentration may range for example from 1 to 30%, preferably from 10 to 20% resulting in a relatively thin liquid. The pore volume of the catalyst matrix is filled with the resultant solution and the solvent is then removed by known means.

BRIEF DESCRIPTION OF THE DRAWINGS

The invention will be better understood from the accompanying drawings illustrating non limitative embodiments of the process, wherein:

FIGS. 3 and 4 show the correlations between the results relating to hydrotreatment catalysts, according to the invention and to the prior art, respectively, and FIGS. 5 and 6 relate to catalytic cracking catalysts and show the correlations between the results according to the invention and those according to the prior art (M.A.T).

Figure 1:
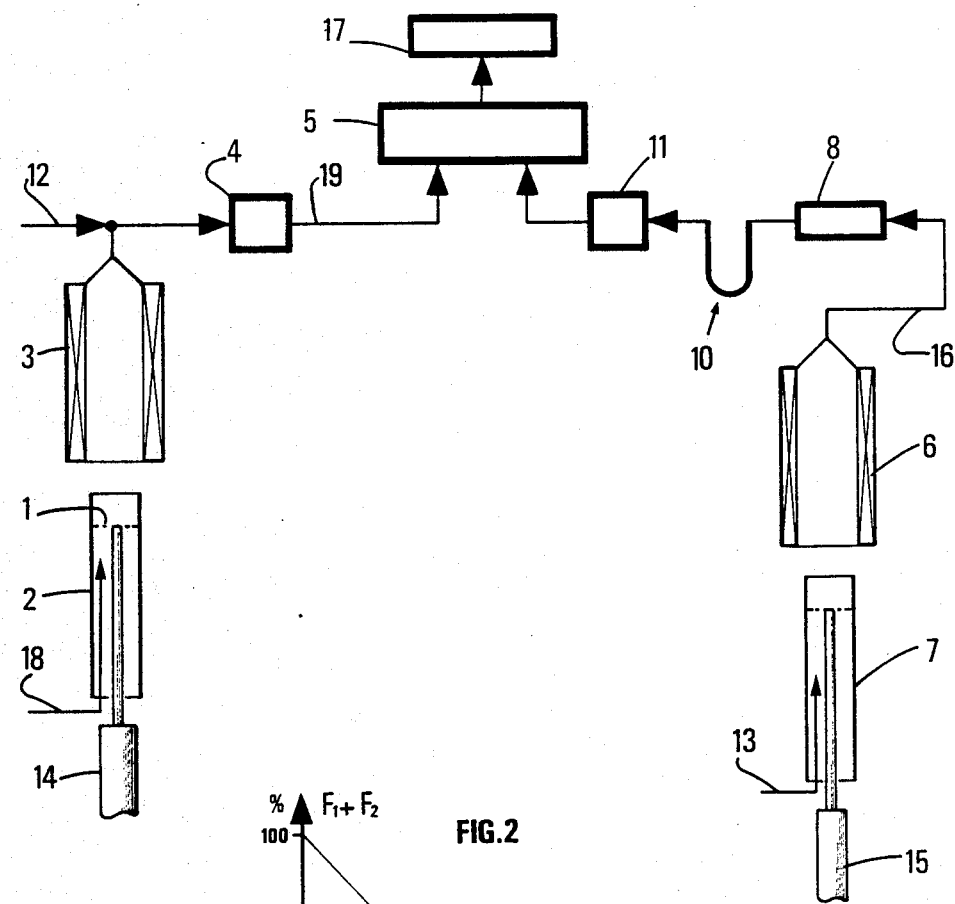
FIG. 1 is a flow sheet diagramatically illustrating means for carrying out the process.

According to FIG. 1 illustrating a particular embodiment of the invention, the catalyst, once impregnated with the hydrocarbon sample, is crushed, then introduced into a boat 1, located at the top of piston 2, actuated by a set of jacks 14. This boat 1 is placed in a first furnace 3 wherein a conversion - evaporation step is performed by heating under a stream 18 of inert gas, for example nitrogen, argon or helium, preferably helium in order to obtain a better response of detector 4.

The inert gas specific flow rate, in proportion to the amount of impregnated porous matrix, is for example from 1 to 50 milliliters per milligram and per minute, preferably from to 10 ml/mg/min.

The heating under the inert gas stream may be conducted as follows:

1. isothermal heating up to 20 min. and preferably to to 5 min. at a temperature $\theta_1$ ranging from room temperature to the prevailing temperature due to the thermal inertia of the furnace once cooled, this temperature $\theta_1$ being at least equal to room temperature, followed by a temperature program, at a rate of temperature increase $V_1$ ranging from 2° C./min. to 50° C./sec., up to a temperature $\theta_2$ of the furnace ranging from 300° C. to 380° C., or 2. a temperature increase from room temperature up to temperature $\theta_2$, at a rate from 2° C./min. to 50° C./sec., or 3. substantially instantaneous temperature increase of the sample from room temperature at its initial state of the above-defined temperature $\theta_2$ of the heated furnace where it is directly introduced.

The effluents from the conversion - evaporation stage are conveyed through a line 19 fed with inert gas 12 and detected during time by means of a hydrocarbon detector, for example a flame ionization detector (FID) 4, previously calibrated with a reference sample. Signal Q may be the object of a single measurement or, when several measurements are performed, the results are integrated by fractions (e.g. one fraction every 1 to 120 seconds, preferably every 40 to 120 seconds) and kept in memory by microprocessor 5. Thus a signal Q is obtained versus time and/or temperature, which is representative of the hydrocarbons generated during said step.

Then pyrolysis is performed, still in a stream of inert gas, using a temperature program from $\theta_2$ to $\theta_3$, temperature $\theta_3$ being higher than $\theta_2$ and ranging for example from 500° C. to 1000° C., preferably from 600° C. to 700° C., at a rate of temperature increase from 2° C./min. to 50° C./sec., preferably from 5° C./min. to 35° C./min.

An isothermal stage is optionally applied, for example during 0.5 to 20 min, when the temperature $\theta_3$ has been reached. This isothermal stage may advantageously last 1–10 minutes.

The pyrolysis effluents are detected by a hydrocarbon detector, for example a flame ionization detector, and the obtained signal P is integrated in the same manner as precedingly discussed and kept in the memory of microprocessor 5.

The boat 1, containing the pyrolysis residue, is then transferred by another piston 7 and another jack 15 to a second furnace 6, advantageously separate from the first one. In this furnace the residue is subjected to combustion under an oxidizing atmosphere, fed through line 13 (air, oxyen or air-oxygen mixture of oxygen content usefully higher than 20%) at a temperature $\theta_4$ from 500° C. to 1500° C., preferably of 600°–700° C., for a time ranging for example from 2 to 20 minutes and more advantageously from 5 to 10 minutes.

The organic carbon present in the residue is converted to carbon dioxide and carbon monoxide and the resultant gas mixture is fed, through line 16, to a catalysis furance 8 at such a temperature that substantially all the carbon monoxide can be converted to carbon dioxide under known-per-se conditions, said furnace containing an oxidation catalyst (e.g. CuO). Carbon dioxide is retained in a trap 10 of liquid nitrogen or solid adsorbant type and then, after it has been released from the trap by known means, it is detected by a specific detector 11, for example a katharometer, which delivers a signal R representative of the residue amount.

This detector 11 may be followed with a series of other detectors, not shown in FIG. 1, specific for the detection of such compounds as sulfur and/or nitrogen which were trapped during the combustion and then released.

The measuring value of signal R is kept in the memory of microprocessor 5.

The integration of the first signal Q resulting from the conversion -evaporation step gives, expressed in milligrams per gram as compared with a standard, the amount of products $A_1$ resulting from the evaporation and conversion during the first heating step. The integration of the second signal P resulting from the pyrolysis step gives the amount of pyrolyzed heavy hydrocarbons $A_2$ in milligrams per gram of sample.

A platinum probe, not shown in FIG. 1, placed in furnace 3 at the sample level, is used for measuring the effective temperature Tmax of the apex of peak $A_2$, which is an information about the pyrolysis procedure.

From an average value of the sample carbon content (from 0.82 to 0.88, e.g. 0.83) it is possible to calculate the organic carbon content resulting from evaporation step $C_Q$ and pyrolysis step $C_P$, for example:

$$C_Q = A_1 \times 0.83$$

$$C_P = A_2 \times 0.83$$

From signal R, and after calibration, the residual carbon weight $C_R$, detected as carbon dioxide, is deduced.

Then the total organic carbon (TOC) is calculated:

$$TOC = C_Q + C_P + C_R$$

Figure 2:
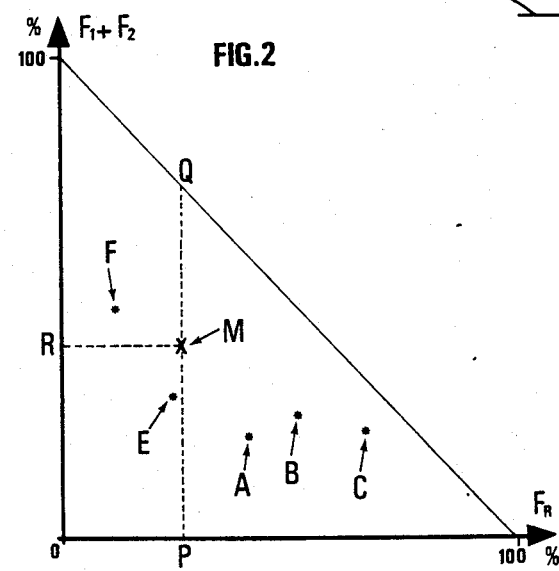
FIG. 2 is a ternary diagram where are plotted $F_R$, $F_2$ and $F_1$ indices, determined as indicated below.

Then the distribution of the products among light fraction ($F_1$), heavy fraction ($F_2$) and coke ($F_r$) may be displayed in a ternary diagram, as shown in FIG. 2, where $F_R$ values are plotted as abscissae and $F_1 + F_2$ values as ordinates. Each given catalyst charge is represented by a point M whose coordinates are:

$$F_1 = \frac{100 \times C_Q}{TOC}$$

$$F_2 = \frac{100 \times C_P}{TOC}$$

$$F_R = \frac{100 \times C_R}{TCC}$$

and $MQ = F_1 \ MP = F_2 \ MR = F_R$

It confirms that the light fraction $F_1$ substantially corresponds to a distillate and the heavy fraction $F_2$ substantially corresponds to the range of vacuum residues.

The process according to the invention meets the above-defined objects. It further makes possible, from a reference feedstock, to explore the behavior of refining catalysts by isolating the effect of one parameter (e.g. the effect of the metal content or of the carrier).

Moreover, the process is reliable, easy to perform and requires only a short analysis period (for example 30–60 minutes).

EXAMPLES

The following examples are given to illustrate the invention and must not be considered as limiting the scope thereof. The first example relates to hydrotreatment and the second to catalytic cracking.

EXAMPLE 1

This example concerns the use of three catalysts A, B and C for hydrotreating residues whose characteristics are reported in Table 1, only the two first catalysts being available on the trade.

TABLE 1

| CATALYSTS | A PROCATALYSE HMC 845 | B PROCATALYSE HMC 841 | C |
|---|---|---|---|
| Total pore volume (m l/g) | 0.90 | 0.90 | 0.70 |
| Specific surface (m 2/g) | 155 | 140 | 300 |
| $MoO_3$ % | 7 | 14 | 20.5 |
| NiO % | 1.5 | 3 | 0 |
| CoO % | 0 | 0 | 4.5 |
| $Al_2O_3$ % | 91.5 | 83 | 75 |

Fresh catalysts A, B and C are subjected to continuous hydrotreatment tests with a charge consisting of Safaniya straight-run residue (S.R.R.) in the following conditions: T=400° C., VVH=0.5 h$^{-1}$, hydrogen pressure = 120 bars, $H_2$ gas/liquid hydrocarbons = 1000 normal liters per liter. The test lasts about 200 hours. The characteristics of the charge are indicated in Table 2. After 200 hours, according to a known technique, the stabilized performances of these catalysts for converting the charge to 500−fraction for example, are expressed by the relationship:

$$500^- \text{ conversion (\%)} = 100 \times \frac{(500^+) \text{ charge} - (500^+) \text{ effluent}}{(500^+) \text{ charge}}$$

TABLE 2

| | Safaniya S.R.R. | Kuwait S.R.R. |
|---|---|---|
| $d_4^{15}$ (g/cm$^3$) | 0.974 | 0.956 |
| S (% by weight) | 4.1 | 3.75 |
| N (ppm) | 2400 | 2000 |
| $nC_7$ asphaltenes (% by weight) | 7 | 2.2 |
| Conradson carbon (% by weight) | 11.9 | 9.2 |
| Viscosity (mm2/s) at 80° C. | 153 | 53 |
| Ni (ppm) | 26 | 20 |
| V (ppm) | 83 | 48 |

After these tests, the catalysts are withdrawn, subjected to extraction in Soxhlet with boiling toluene for 12 hours, and dried at 80° C. for 6 hours. The residual carbon content is then determined on the samples. This carbon, insoluble in toluene, is assimilated to catalytic "coke". The results of these measurements are reported in Table 3.

TABLE 3

| Catalyst | 500 conversion % | coke % |
|---|---|---|
| A | 41.3 | 12.0 |
| B | 39.7 | 13.8 |
| C | 34.1 | 20.6 |

Simultaneously, other samples of A, B and C fresh catalysts are subjected to micropyrolysis tests according to the invention: they are previously impregnated with a 10% by weight solution of Safaniya straight run residue (S.R.R.) in toluene.

Toluene is evaporated under vacuum at 80° C. for 2 hours.

Each catalyst (30 mg) is then crushed and introduced into a boat of stainless steel. The boat is placed into a first furnace maintained in helium flow of 100 ml/min, at a temperature of 300° C. for 3 minutse. The effluents are detected by a flame ionization detector, the signal is integrated according to the invention every 120 seconds and the results kept in the microprocessor memory. Then the temperature is increased by a rate of 30° C./min, up to 600° C. The pyrolysis effluents are detected by the flame ionization detector and the pyrolysis signal integrated every 120 seconds and kept in memory; then a combustion is performed by placing the boat containing the sample into a second furnace, under air and oxygen atmosphere at a flow rate of 350 ml/min and at a temperature of 600° C. for about 7 minutes. The oxides resulting from the combustion, particularly carbon monoxide and dioxide are then conveyed to a catalysis furnace filled with copper oxide and heated to about 400° C., so as to convert substantially all the carbon monoxide to carbon dioxide. All the carbon dioxide is then trapped over molecular sieve of 5 Å ($5 \times 10^{-10}$m). At the end of the combustion step, the trap is purged and carbon dioxide is detected by katharometer.

Respective $F_1$, $F_2$ and $F_R$ indices, calculated according to the invention, are reported in Table 4 and in FIG. 2.

TABLE 4

| Cata-lyst | $F_1$ Kuwait S.R.R | $F_1$ Safaniya S.R.R | $F_2$ Kuwait S.R.R | $F_2$ Safaniya S.R.R | $F_R$ Kuwait S.R.R | $F_R$ Safaniya S.R.R |
|---|---|---|---|---|---|---|
| A | 37.4 | 36.0 | .23.4 | 21.0 | 39.2 | 43.0 |
| B | 26.0 | 23.5 | 25.0 | 22.5 | 49.0 | 54.0 |
| C | 12.0 | 8.0 | 24.5 | 23.0 | 63.5 | 69.0 |

FIGS. 3 and 4 illustrate correlations obtained, with hydrotreatment catalysts A, B and C, between the results according to the invention and long test results. As a matter of fact, in FIG. 3, the conversion to 500− fraction measured at the end of the long test is plotted as ordinate and $F_1$ index according to the invention as abscissa, whereas in FIG. 4, the coke percentage, after hydrotreatment according to the known method of the prior art, is plotted as ordinate and the coke index $F_R$ according to the invention as abscissa. The good correlation shows the validity of the test according to the invention which may accordingly be validly used to appreciate the conversion and coking activities of different catalysts.

EXAMPLE 2

Example 1 is repeated, except that the Safaniya charge is replaced with a Kuwait straight-run residue (S.R.R.) whose characteristics are given in Table 2. Parameters $F_1$, $F_2$ and $F_R$ according to the invention are given in Table 4 for each catalyst A, B and C.

It is observed from table 4 that, when a straight-run residue of slightly different characteristics is used according to the invention, the obtained catalyst classification is unchanged. The observed correlations are still valid.

EXAMPLE 3

This example concerns two catalytic cracking catalysts.

A pure silica F of 200 m²/g specific surface is compared with a catalyst E of the trade, previously subjected to a 2 hour treatment at 800° C. under 1 atmosphere of steam (DA 250 of Grace Davison). The M.A.T. test (Micro-Activity-Test), according to standard D 39-07, is used as reference test. The charge in M.A.T. tests is a mixture comprising 30% of Kirkuk straight-run residue (S.R.R.) +70% of Kirkuk vacuum distillate (V.D.) whose characteristics are reported in Table 5.

TABLE 5

| $d_4^{15}$ | 0.9352 |
|---|---|
| S | 2.63% |
| Conradson carbon | 2.87% |
| $nC_7$ asphaltenes | 0.2% |
| Distillation | |
| 5% | 305° C. |
| 50% | 465° C. |
| 90% | 575° C. |

The M.A.T. test results are reported in Table 6.

TABLE 6

| M.A.T. balance | DA 250 | Pure Silica |
|---|---|---|
| Conversion (%) | 60.7 | 6.4 |
| Total gas (% b.w.) | 13.4 | 3.6 |
| $C_5$-221° C. gasoline (% b.w.) | 39.7 | 2.6 |
| 221–350° C. gas oil (L.C.O.) (% by weight) | 17.9 | 4.7 |
| 350° C. liquid residue (% b.w.) | 21.2 | 88.8 |
| Coke (% b.w.) | 7.6 | 1.4 |

The same catalysts are subjected to a test according to the invention. They are impregnated with a 10% by weight solution of Kuwait S.R.R. in toluene.

Toluene is evaporated for 2 hours under primary vacuum at 80° C.

TABLE 7

| | DA 250 E | Pure Silica F |
|---|---|---|
| $F_1$ (% b.w.) | 46.3 | 42.6 |
| $F_2$ (% b.w.) | 29.8 | 47.0 |
| $F_R$ (% b.w.) | 23.9 | 10.4 |

The impregnated samples are subjected to micropyrolysis as described in example 1. The results are reported in Table 7 and in FIG. 2 giving the values of $F_1$, $F_2$ and $F_R$ indices.

Two correlation examples are illustrated in FIGS. 5 and 6. In order to more precisely show the correlation, the same charge has een treated with two other catalysts G and H both according to the invention process and the M.A.T. test, above-described in this example. Catalyst G is an alumino-silicate whereas catalyst H is a trade catalyst DA 250 of Grace Division doped with 0.5% by weight of nickel. In FIG. 5, the 350+fraction obtained according to the prior art (M.A.T.) has been plotted as ordinate and $F_2$ index, obtained by the process according to the invention, as abscissa. Similarly, in FIG. 6, the coke percentage according to the prior art has been plotted as ordinate and the coke index $F_R$ according to the invention as abscissa.

A good correlation between the method of the invention and the M.A.T. test is observed.

What is claimed as the invention is:

1. A process for characterizing a porous catalyst by determination of its hydrocarbon conversion and coking activities, comprising the successive steps of:
   (a) impregnating the catalyst with a hydrocarbon mixture provided in a thin liquid form permitting the pore of the catalyst to be filled,
   (b) heating the impregnated catalyst, in a stream of an inert gas, up to a temperature $\theta_2$ ranging from 300° C. to 380° C., so as to produce a conversion - evaporation during this step of temperature increase, thereby separating out a conversion - evaporation effluent, (c) subjecting said conversion - evaporation effluent, during the heating step, to a measurement, with a hydrocarbon detector, of a signal Q representative of the hydrocarbons generated during said conversion - evaporation step, (d) progressively increasing the temperature of resultant impregnated catalyst freed of said conversion - evaporation effluent from $\theta_2$ at a rate of temperature increase ranging from 2° C./min. to 50° C./sec to a value $\theta_3$ ranging from 500° C. to 1000° C., under an inert gas stream, so that pyrolysis occurs during said heating step, thus producing a pyrolysis effluent and a residue, (e) subjecting said pyrolysis effluent, during the heating step, to a measurement, by means of a hydrocarbon detector, of a signal P representative of pyrolyzed hydrocarbons generated during said pyrolysis step, (f) subjecting said residue to combustion at a temperature $\theta_4$ ranging from 500° C. to 1500° C., under a stream of oxidizing gas, said combustion producing a combustion gas effluent.

(g) subjecting said combustion gas effluent, by means of at least one suitable detector, to measurement of a signal R representative of the residue amount, and (h) deducing by signal processing means from said measured values of signals P, Q and R the conversion and coking activities of said catalyst.

2. A process according to claim 1, wherein the catalyst is impregnated with a 1-30% by weight solution of the hydrocarbon mixture dissolved in a solvent having a boiling point lower than the initial boiling point of the hydrocarbon mixture, the solvent being then removed.

3. A process according to claim 1, wherein in step (b) the impregnated catalyst is heated from room temperature to said temperature $\theta_2$, at a rate of temprature increase ranging from 2° C./min. to 50°C./sec.

4. A process according to claim 1, wherein in step (c) a series of signals is measured during the conversion - evaporation step, said signals being integrated at every 1 to 120 s so as to obtain said signal Q.

5. A process according to claim 1, wherein a series of signals are measured during the pyrolysis step, said series of signals being integrated at every 1 to 120 sec. 2 so as to obtain said signal P.

6. A process according to claim 1, wherein said steam of inert gas used in steps (a) and (d) has a specific flow rate expressed in proportion to the amount of porous matrix from 1 to 50 milliliters per milligram and per minute.

7. A process according to claim 1, wherein said combustion is performed in a range of 2-20 minutes.

8. A process according to claim 1, wherein the catalyst in step (f) is heated to 600° C. to 700° C. for a time ranging from 5 to 10 minutes.

9. A process according to claim 1, wherein the catalyst is a cracking catalyst.

10. A process according to claim 1, wherein the catalyst is a hydrotreatment catalyst.

11. A process according to claim 1, wherein said $\theta_3$ is at least 600° C.

12. A process according to claim 1, wherein the catalyst is heated at a rate of temperature increase of from 5° C./min to 35° C./min during said pyrolysis step.

13. A process according to claim 12, wherein $\theta_3$ is 600°-700° C.

14. A process according to claim 1, wherein said suitable detector of step (g) is a specific detector for carbon dioxide.

15. A process according to claim 14, step (g) further comprising subjecting said combustion gas effluent to measurement with a specific detector for sulfur and/or nitrogen compounds.

16. A process according to claim 14, wherein the $CO_2$ detector is a katharometer.

* * * * *